United States Patent
Kraus

(10) Patent No.: US 8,506,628 B2
(45) Date of Patent: *Aug. 13, 2013

(54) OSSICULAR PROSTHESIS HAVING HELICAL COIL

(75) Inventor: Eric M. Kraus, Greensboro, NC (US)

(73) Assignee: Enteroptyx, Memphis, TN (US)

( * ) Notice: Subject to any disclaimer, the term of this patent is extended or adjusted under 35 U.S.C. 154(b) by 99 days.

This patent is subject to a terminal disclaimer.

(21) Appl. No.: 13/295,725

(22) Filed: Nov. 14, 2011

(65) Prior Publication Data

US 2012/0123538 A1    May 17, 2012

Related U.S. Application Data

(62) Division of application No. 12/026,912, filed on Feb. 6, 2008, now Pat. No. 8,057,542.

(51) Int. Cl.
*A61F 2/18*    (2006.01)

(52) U.S. Cl.
USPC ................................................. 623/10

(58) Field of Classification Search
CPC .................................. A61F 2/18; H04R 25/00
USPC ............................................ 623/10; 600/25
See application file for complete search history.

(56) References Cited

U.S. PATENT DOCUMENTS

| | | |
|---|---|---|
| 3,710,399 A | 1/1973 | Hurst |
| 3,722,003 A | 3/1973 | Walchle |
| 4,601,723 A | 7/1986 | McGrew |
| 4,624,672 A | 11/1986 | Lenkauskas |
| 5,061,280 A | 10/1991 | Prescott |
| 5,104,401 A | 4/1992 | Kurz |
| 5,514,177 A | 5/1996 | Kurz et al. |
| 5,554,188 A | 9/1996 | Prescott |
| 5,935,167 A | 8/1999 | a Wengen |
| 6,168,625 B1 | 1/2001 | Prescott |
| 6,277,148 B1 | 8/2001 | Dormer |
| 6,387,128 B1 | 5/2002 | Kurz et al. |
| 6,436,031 B1 | 8/2002 | Salib |
| 2007/0055372 A1 | 3/2007 | Prescott et al. |
| 2007/0255405 A1 | 11/2007 | Reitan et al. |

FOREIGN PATENT DOCUMENTS

| | | |
|---|---|---|
| EP | 0224080 | 7/1992 |
| GB | 2275422 | 8/1994 |

*Primary Examiner* — Andrew Iwamaye
(74) *Attorney, Agent, or Firm* — Gordon & Jacobson, PC

(57) ABSTRACT

An ossicular prosthesis includes a proximal end provided with an open conically helical coil for engaging a first ossicular structure, and a distal bell head, piston, or shoe for engaging a second ossicular structure. A connecting element extends therebetween the two to hold the helical coil structure which engages the second ossicular engagement structure in a preferably fixed relationship. The helical coil defines a plurality of spaced apart adjacent windings, with open spaces between the windings. Each adjacent winding decreases in diameter from the proximal to distal end. The windings of the coil may be adjusted relative to each other in length or angle to fit the anatomy. In accord with a one method of use, the helical coil and optionally other portions of the prosthesis function as an armature or endoskeleton. A cement may be provided over the prosthesis to reconstruct the eroded or missing ossicles.

17 Claims, 14 Drawing Sheets

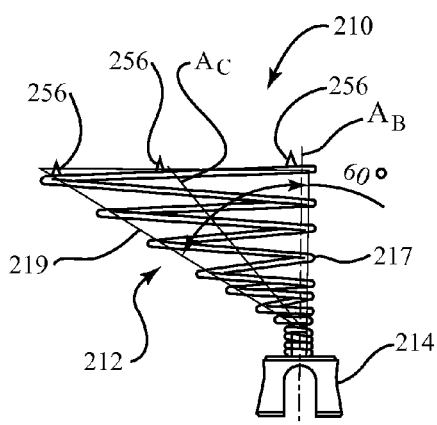
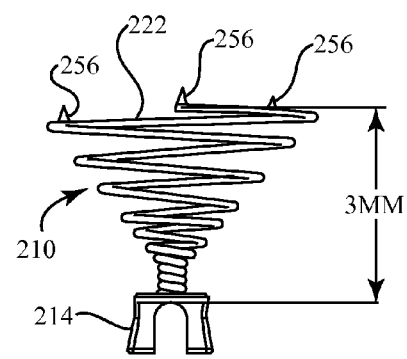
*Fig. 18*  *Fig. 19*
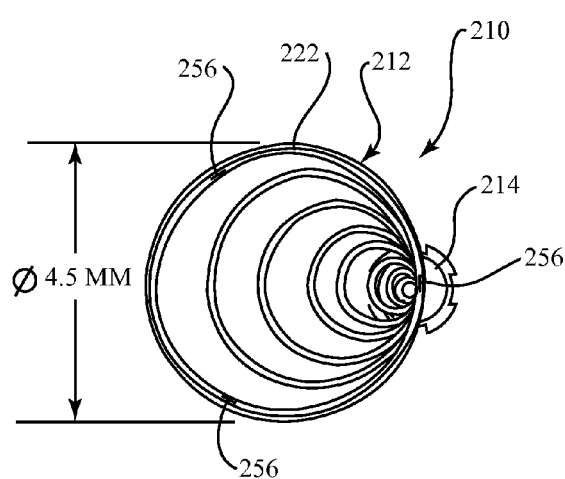
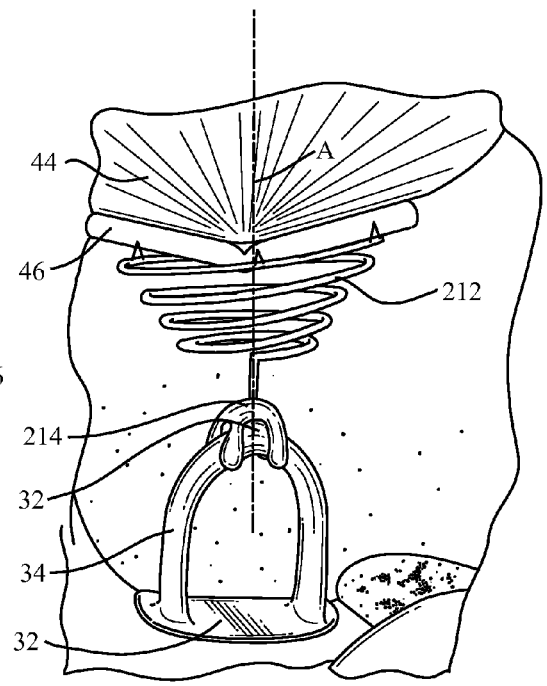
*Fig. 20*  *Fig. 21*

OSSICULAR PROSTHESIS HAVING HELICAL COIL

CROSS-REFERENCE TO RELATED APPLICATION

This application is a divisional of U.S. Ser. No. 12/026,912, filed Feb. 6, 2008, and now issued as U.S. Pat. No. 8,057,542, which is hereby incorporated by reference herein in its entirety.

BACKGROUND OF THE INVENTION

1. Field Of The Invention

This invention relates broadly to prostheses. More particularly, this invention relates to prostheses for the middle ear for replacement, in whole or in part, of one or more ossicles.

2. State Of The Art

Hearing is facilitated by the tympanic membrane transforming sound in the form of acoustic sound waves within the outer ear into mechanical vibrations through the chain of ossicular bones (malleus, incus, stapes) in the middle ear. These vibrations are transmitted through the ossicular bones to the footplate of the stapes where micro or macro motion of this structure results in compression waves within the fluid of the inner ear. These compression waves lead to vibrations of the cilia (hair cells) located within the cochlear where they are translated into nerve impulses. The nerve impulses are sent to the brain via the cochlear nerve and are interpreted in the brain as sound.

Hearing efficiency can be lost to erosion of the ossicular bones. Various combinations or portions of the bones can be replaced. For example, the malleus and incus can be replaced leaving all or a portion of the stapes intact or the incus and stapes can be replaced leaving all or a portion of the malleus intact. Such a procedure is a partial ossicular replacement prosthesis, or PORP. Alternatively, the incus, malleus and stapes can be completely replaced by a prosthesis in a procedure referred to as a total ossicular replacement prosthesis, or TORP.

In addition, for implantation of certain middle ear transducer hearing devices, a majority of the long process (long arm) of the incus is removed during the procedure. If explantation of the hearing device is later required, it is necessary to reattach the incus to the stapes. Current incudo-stapedial joint (ISJ) prostheses may not have sufficient length to effectively span the gap between the remaining incus and the stapes capitulum.

Further, most incudo-stapedial joint prostheses, whether implanted due to erosion or post-explantation reconstructions, are designed with claws that are difficult to orient, require crimping, and may lead to delayed pressure necrosis of the ossicles to which it is attached. Other incudo-stapedial joint prostheses that require positioning of the prosthesis between the eroded incus and stapes capitulum are often unstable and are only effective for reconstructing small gaps between the eroded incus and stapes. Incudo-stapedial reconstruction using autograft bone chips or cartilage tend to deteriorate over time. The result is reoccurrence of ossicular discontinuity and decreased hearing.

SUMMARY OF THE INVENTION

In accord with the invention, an ossicular prosthesis includes an open helical coil for engaging a first ossicular structure, an engagement structure which engages a second ossicular structure, and a connecting element extending therebetween to hold the helical coil and engagement structure in a fixed relationship.

The helical coil defines a plurality of spaced apart windings, with open spaces between the windings. The coil has a proximal first end with a preferably largest diameter and a distal second end with a preferably smallest diameter. As such, each adjacent winding decreases in diameter from the proximal to distal end. The windings of the coil may be adjusted relative to each other to fit the anatomy. Particularly, the coil can be plastically deformed to adjust the diameter of at least one winding. The engagement structure may include a bell head adapted to engage the stapes at the capitulum, or a piston or shoe for engaging the stapes footplate. The connecting element between the coil and engagement structure may include an angled or straight strut, and may also include a second coiled element to further facilitate adjustment of the prosthesis and alignment of the remaining ossicles.

The prosthesis is preferably manufactured from a titanium. Such material is MRI compatible. The titanium may be porous. In accord with a one manner of use, the helical coil and optionally other portions of the prosthesis function as an armature or endoskeleton and are provided with a cement, such as a glass ionomeric cement or hydroxylapatite cement.

According to embodiments of the invention adapted for use where the malleus and a portion of the incus are present, the conical helical coil is sized to be received over a portion of the incus. The engagement structure may include either a bell head angled relative to the conical coil to seat on the capitulum of the stapes superstructure or a piston angled relative to the coil for engaging the stapes footplate (when the stapes superstructure is missing). The piston may engage the surface of a mobile stapes footplate or may be engaged into a footplate stapedostomy (an opening created through the footplate) if the footplate is immobile. Optionally, the coil, connecting element, and engagement structure define an armature or endoskeleton for a cement. The endoskeleton provides strength, increased surface area for cement bonding, and directionality for the cement.

According to embodiments of the invention adapted for use where the malleus is present but the incus is absent, the proximal first end of the helical coil is bent relative to the second end of the helical coil to define a space in which the malleus is received. The malleus is received by a combination of inter-coil tension and friction fit and without disturbing the adjacent tympanic membrane. The engagement structure on such embodiment may include a bell head angled relative to the coil to seat on the capitulum of the stapes or a piston angled relative to the coil for engaging the stapes footplate. The piston may engage the surface of a mobile stapes footplate or may be engaged in a footplate stapedostomy, if the footplate is immobile. Optionally, the helical coil and engagement structure can be used as an armature or endoskeleton for a cement.

According to embodiments of the invention adapted for use where the malleus and incus are absent, the prosthesis is suitable for use between the tympanic membrane and the stapes, stapes footplate, or oval window. The open helical coil has a central axis oriented parallel to, and preferably offset from, a bell, piston, or shoe. The first end of the coil is optionally provided with one or more spikes to facilitate retention of cartilage between the proximal first end of the coil and the tympanic membrane or a tissue graft used to reconstruct the tympanic membrane. Optionally, the coil and engagement structure can be used as an armature or endoskeleton for a cement.

In all the embodiments, the open wound conical coil permits the prosthesis to be adjusted in length and width in the operating room so as to fit any shape and angle of the existing anatomy. In applicable embodiments, the helical shape also permits a straightforward slide-on placement of the prosthesis over the proximal end of the incus and eliminates awkward claws, the need for crimping and delayed pressure necrosis of the incus. Moreover, it has been found that the auditory characteristics of a reconstructed ossicular chain using the prostheses compare favorably to an intact ossicular chain.

Additional objects and advantages of the invention will become apparent to those skilled in the art upon reference to the detailed description taken in conjunction with the provided figures.

BRIEF DESCRIPTION OF THE DRAWINGS

FIG. 18 is a side elevation of a third embodiment of an ossicular prosthesis according to the invention.

FIG. 19 is a view of the third embodiment rotated 90° from FIG. 18.

FIG. 20 is a top view of the third embodiment of the invention.

FIG. 21 illustrates implantation of the third embodiment of the ossicular prosthesis between the tympanic membrane and capitulum of the stapes, with the implant shown rotated 90° relative to the orientation shown in FIG. 18.

DETAILED DESCRIPTION OF THE PREFERRED EMBODIMENTS

Figure 1A:
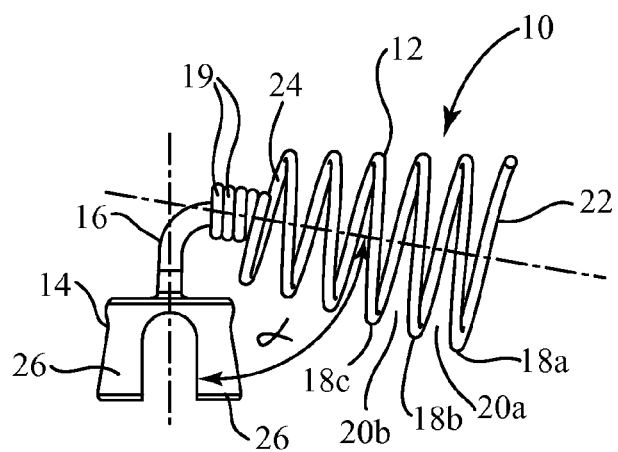
FIG. 1A is a side elevation view of a first embodiment of an ossicular prosthesis for reconstruction of the incudo-stapedial chain.
Figure 1B:
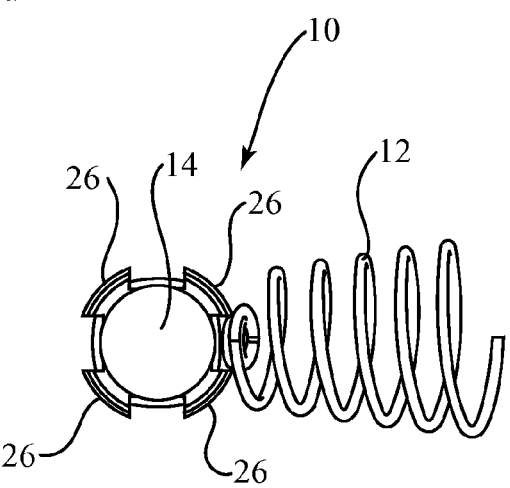
FIG. 1B is a bottom view of the embodiment shown in FIG. 1A.

Turning now to FIG. 1A, a first embodiment of an ossicular prosthesis 10 is shown. The prosthesis 10 includes a stiff conical, helical coil 12 for engaging a first ossicular structure, a bell head 14, and a strut 16 connecting the bell head 14 to the helical coil 12. The entirety of the prosthesis 10 is preferably manufactured from a titanium. Such material is strong, has low density, is well tolerated by middle ear tissue, and is magnetic resonance imaging (MRI) compatible. The material may optionally be porous.

More particularly, the conical, helical coil 12 defines a plurality of spaced apart adjacent windings, e.g., 18a, 18b, 18c with open spaces, e.g., 20a, 20b, between the windings. In preferred embodiments, coil 12 includes 5 to 8 windings of a titanium wire. The coil 12 has a proximal first end 22 with a preferably largest diameter and a distal second end 24 with a preferably smallest diameter. As such, each adjacent winding preferably decreases in diameter from the first to second ends. The coil 12 is preferably approximately 3 mm in length between the first and second ends 22, 24.

Figure 2:
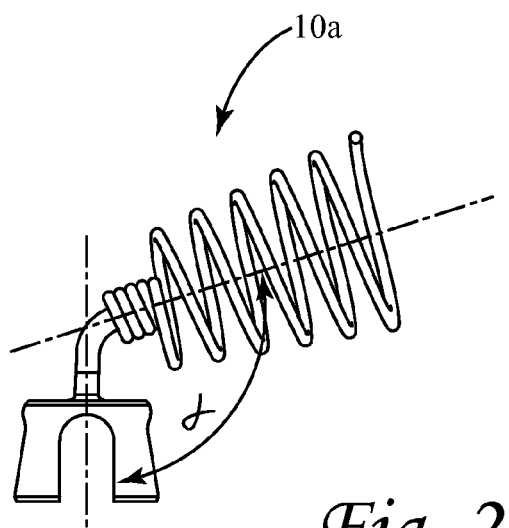
FIG. 2 is a side elevation of an alternate first embodiment of an ossicular prosthesis for reconstruction of the incudo-stapedial chain.

The bell head 14 includes a rigid or deformable framework for engaging the stapes superstructure; i.e., the anterior crus, posterior crus, neck, and capitulum. In a preferred embodiment, the framework includes four flanges 26. The flanges 26 can be adjusted to accommodate different sized stapes capitula. The strut 16 extends upward from the bell head and is connected to the coil 12. The strut 16 is bent at an angle ($\alpha$ preferably equals 80° to 130°), with an acute 80° angle shown in FIG. 1A. As shown with respect to prosthesis 10a in FIG. 2, angle $\alpha$ can be an obtuse angle, e.g., 100°. Angle $\alpha$ corresponds to the angle between the longitudinal axis of the coil 12 and the central axis of the bell head 14. The strut 16 may be a discrete element connected to the bell head 14 and to one or more supplemental windings 19 at the second end 24 of the coil 12. The supplemental windings 19 may extend in a cylindrical or conical helix. The strut 16 preferably extends approximately 0.5 mm above the bell head 14, is then angled at angle $\alpha$, and then extends another approximately 1.5 mm to the second end 24 of the coil 12. The strut 16 operates to hold the coil 12 and bell head 14 in an anatomical relationship. Alternatively, the strut 16 may be formed integrally with the second end 24 of the coil.

Figure 3:
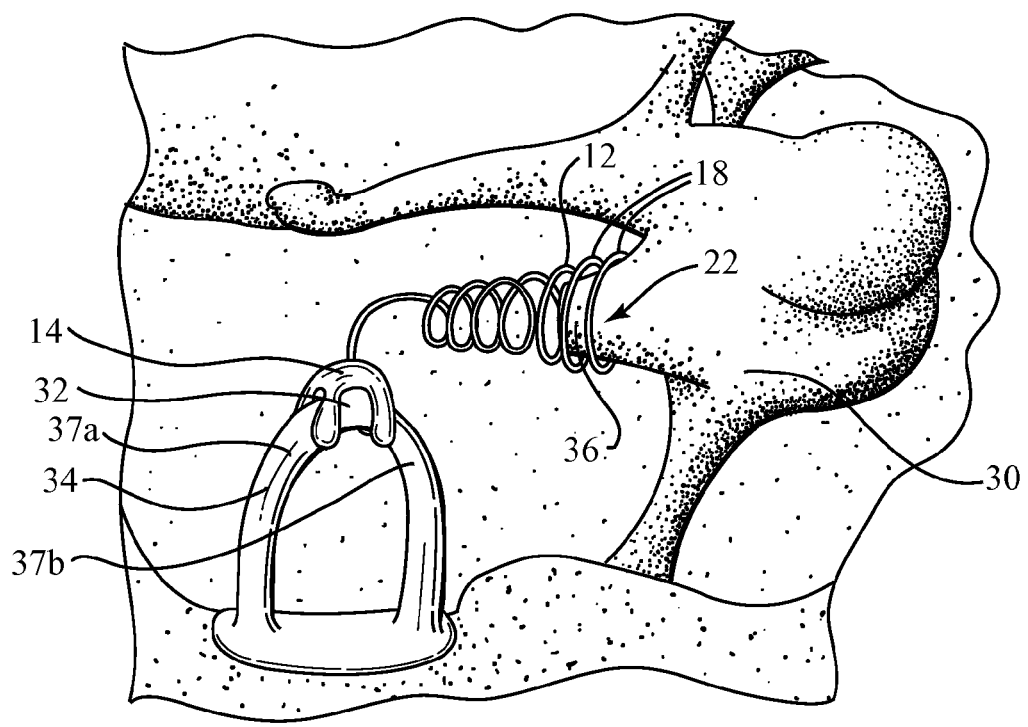
FIG. 3 illustrates implantation of either of the first embodiment of the ossicular prosthesis between the long process of the incus and the stapes capitulum.

Referring to FIG. 3, the prosthesis 10 is used to reconstruct the ossicular chain between the incus 30 and the capitulum 32 of the stapes 34, particularly where a large portion of the long process 36 of the incus 30 is eroded or missing. The larger diameter first end 22 of the coil 12 is placed over the intact portion of the long process 36. The bell head 14 is placed over the capitulum 32 of the stapes 34. If the capitulum is missing, the bell head is seated on the stapes crura 37a, 37b. The windings 18 of the coil 12 may be adjusted by plastic deformation relative to each other (to adjust the coil in total length) and the strut 16 may be plastically deformed (or bent) in angle to better fit the anatomy so that the windings of the coil are relatively evenly spaced apart, any incudo-stapedial gap is bridged, and the anatomy is held in a proper relationship. No crimping is required during the implantation.

Figure 4:
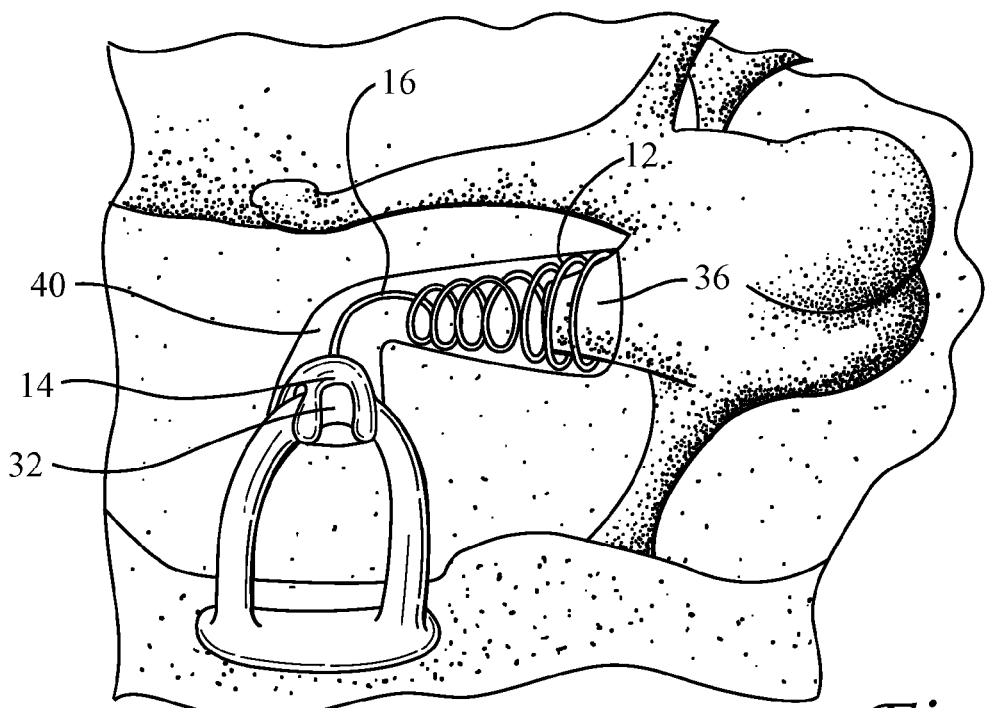
FIG. 4 illustrates the implanted prosthesis of FIG. 3 covered in a cement.

Turning to FIG. 4, according to an optional method of reconstructing the ossicular chain, the helical coil 12 and optionally the strut 16 and/or bell head 14 function as an armature or endoskeleton for a suitable cement 40. The cement is preferably a glass ionomeric cement or hydroxylapatite cement. In accord with such method, the cement is provided over the prosthesis to effectively form a reconstructed incus about the prosthetic armature. In the procedure, the cement 40 is pre-coated on the ossicles; i.e., the incus 32 and stapes capitulum 36, the prosthesis 10 is provided onto the pre-coated ossicles, and the prosthesis is covered in cement 40. The open spaces between the windings provide space for the cement to be received. Good results have been obtained with glass ionomeric cement, such as EnvoyCem™, available from Envoy Medical Corporation, St. Paul, Minn. In various embodiments of the procedure, (i) no cement is used, (ii) the cement is applied as only a pre-coat to the ossicle(s) prior to coupling the prosthesis thereover, (iii) only the proximal helical coil is coated in cement, with the distal bell head remaining uncemented, and (iv) the entire prosthesis is coated in cement.

Figure 5:
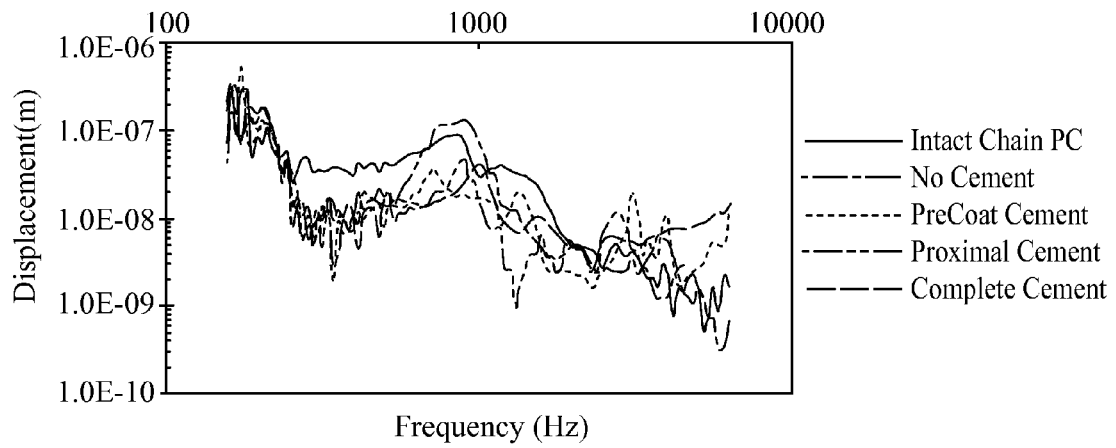
FIG. 5 graphs displacement versus frequency in response to a 100 dB SPL sound stimulus for laser doppler vibrometry measurements at the stapes for the implanted first embodiment of the invention, with and without cement, as compared to measurements of the intact ossicular chain, in a fresh frozen human temporal bone.
Figure 6:
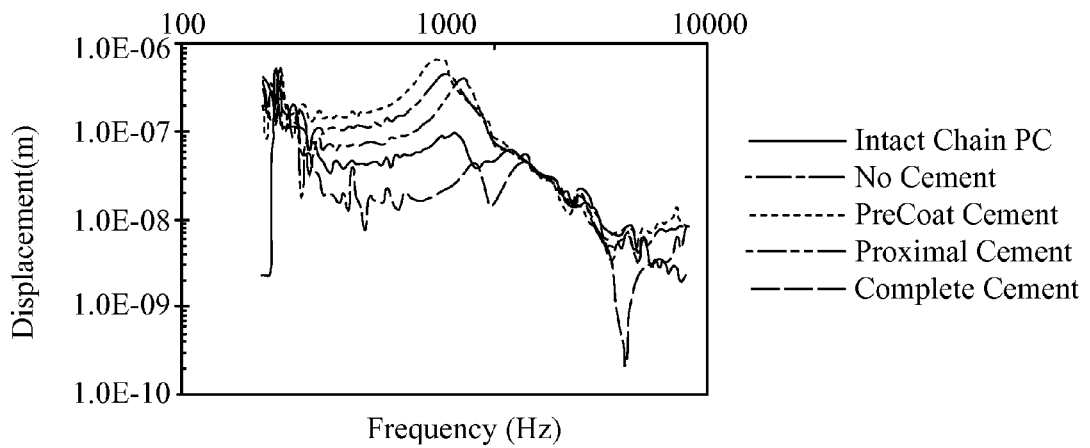
FIG. 6 graphs displacement versus frequency in response to a 100 dB SPL sound stimulus for laser doppler vibrometry measurements at the incus for the implanted first embodiment of the invention, with and without cement, as compared to measurements of the intact ossicular chain, in a fresh frozen human temporal bone.

Referring now to FIGS. 5 and 6, to test the responsiveness of the prosthesis 10a, laser doppler vibrometry tests were performed comparing the prosthesis (without cement and in various states of cementing: pre-coat cement, proximal and distal cement, and complete cement) to an intact ossicular chain. The tests compared the displacement at various frequencies at 100 dB SPL sound stimulus applied to the ear canal. Measurements were made at the stapes (FIG. 5) and at the incus (FIG. 6). It is initially evident that the measurements of the prosthesis, with and without cement, tracked the intact ossicular chain very well. The relative movement at the various frequencies indicate that the performance of the prosthesis in each of the implantable iterations, while slightly different, is very good.

Figure 7:
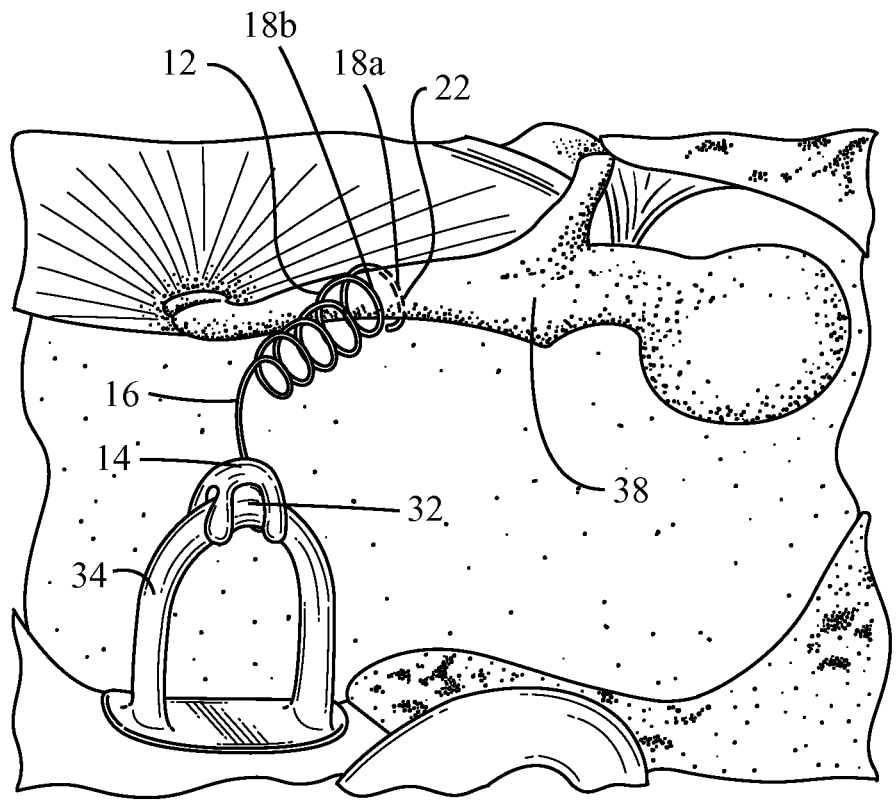
FIG. 7 illustrates implantation of the first embodiment of the ossicular prosthesis between the malleus and the stapes capitulum.
Figure 8:
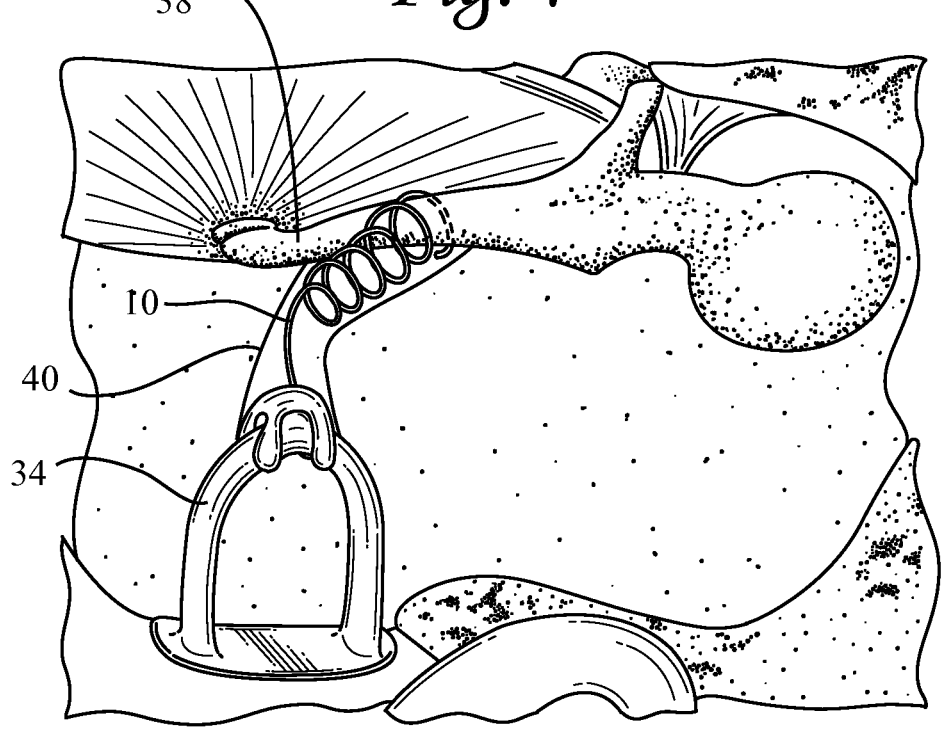
FIG. 8 illustrates the implanted prosthesis of FIG. 7 covered in a cement.

Turning now to FIG. 7, when the incus is missing and the stapes footplate is mobile, the prosthesis 10 can be used to reconstruct the ossicular chain between the malleus 38 and the capitulum 32 of the stapes 34. The windings 18a, 18b at the larger diameter first end 22 of the coil 12 are spread open and placed over the malleus 38. Windings 18a, 18b engage with the malleus by inter-coil forces and friction fit. The adjacent tympanic membrane is not disturbed. The bell head 14 is placed over the capitulum 32 or crura of the stapes 34. No crimping is required during implantation. The windings 18a, 18b may need to be opened and the strut 16 may need to be re-angled by the surgeon (e.g., $\alpha$=80° to 160°), or an embodiment of the prosthesis may be manufactured for such implantation with the windings opened and/or the strut set at the required angle. Referring to FIG. 8, the prosthesis 10 may also be cemented relative to the malleus 38 and/or stapes 34 with cement 40, generally as described above.

Figure 9A:
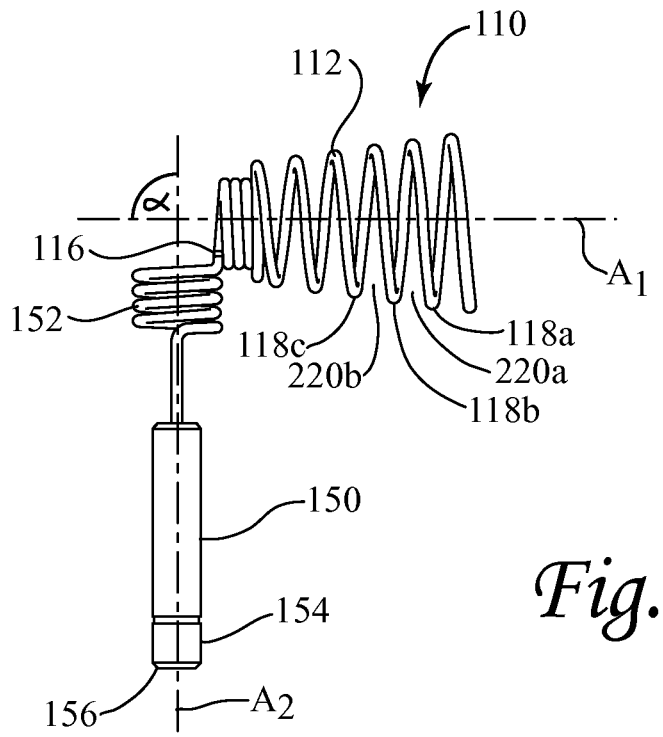
FIG. 9A is a side elevation of a second embodiment of an ossicular prosthesis for reconstruction of the incudo-stapedial chain.
Figure 9B:
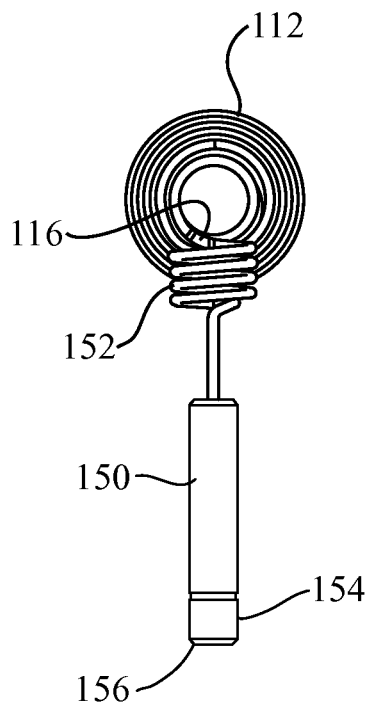
FIG. 9B is an end view of the embodiment shown in FIG. 9A.

Turning to FIGS. 9A and 9B, another embodiment of a prosthesis 110 according to the invention is shown. The prosthesis 110 includes a proximal portion with a conical helical first coil 112 having an axis $A_1$. First coil 112 is substantially similar to coil 12 (FIG. 1A). Conical helical coil 112 defines a plurality of spaced apart adjacent windings e.g. 118a, 118b, 118c with open spaces e.g. 220a, 220b between the windings. The prosthesis includes a distal portion having a cylindrical piston 150 and a second coil 152 preferably arranged in axial alignment with each other along axis $A_2$. Axes $A_1$ and $A_2$ are angled relative to each other ($\alpha$=80° to 160°). The first coil 112 and second coil 152 are preferably continuous by way of a connecting winding 116 that bends through angle $\alpha$. Alternatively, a strut may connect the proximal and distal portions of the prosthesis. The distal portion of cylindrical piston 150 includes circumferential groove 154 located 0.5 mm from the distal portion 156 to guide the depth of insertion of the distal portion 156 into a footplate stapedostomy.

Figure 10:
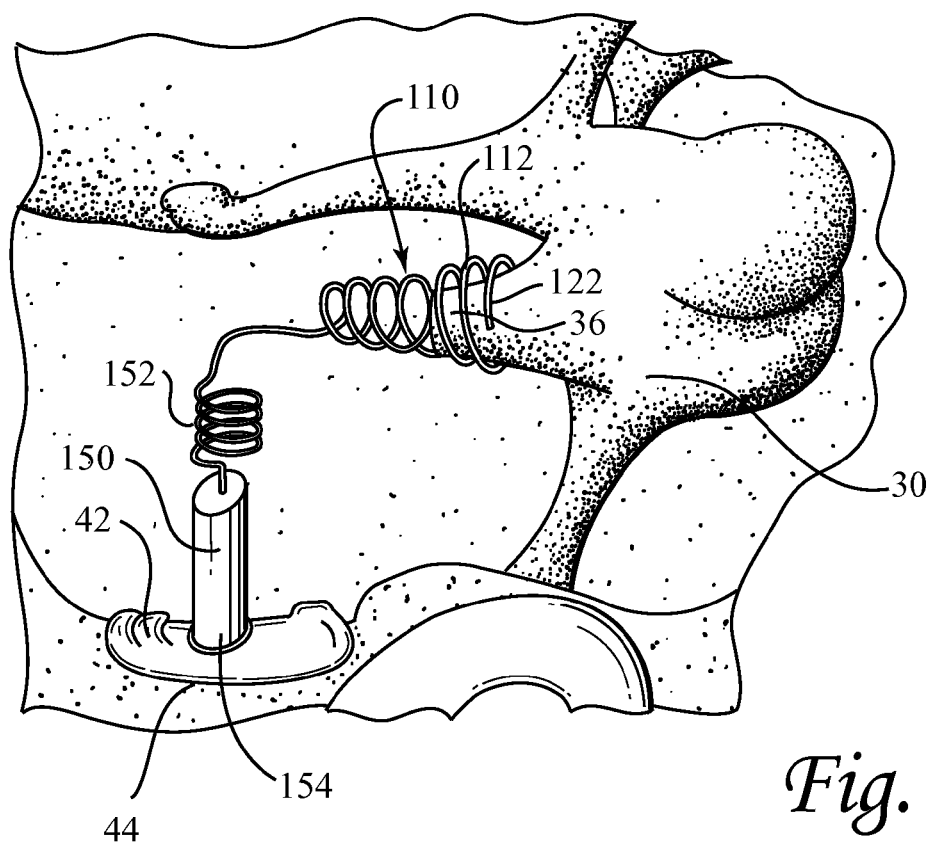
FIG. 10 illustrates implantation of the second embodiment of the ossicular prosthesis between the incus and the stapes footplate.
Figure 11:
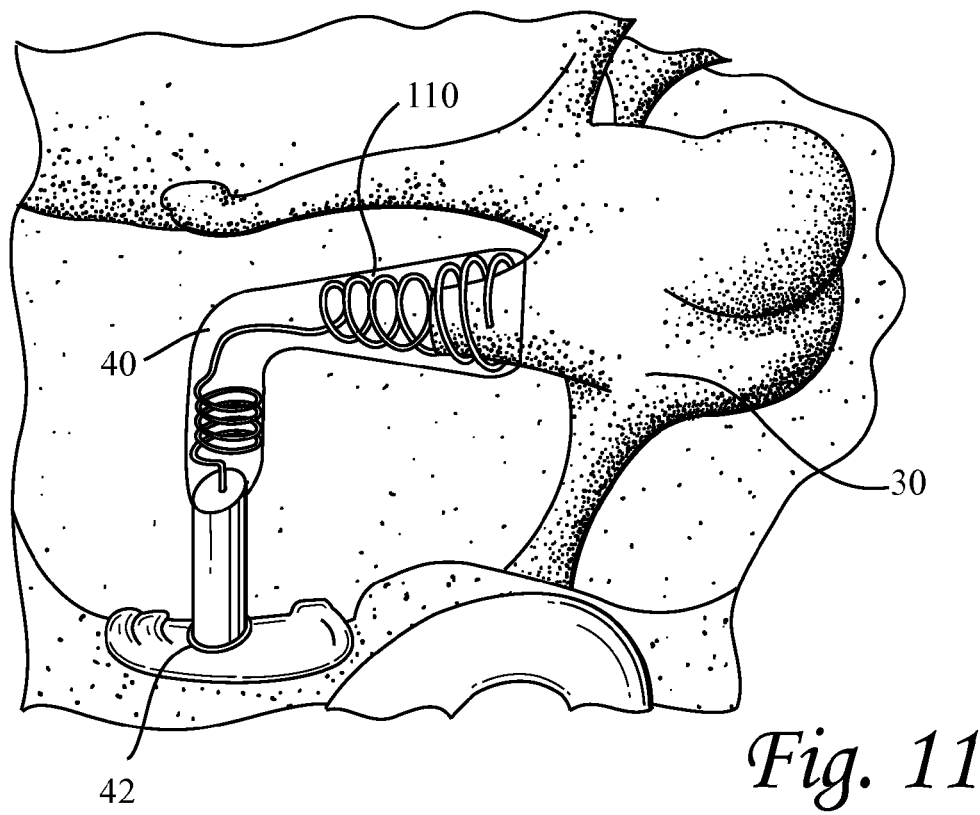
FIG. 11 illustrates the implanted prosthesis of FIG. 10 covered in a cement.

Turning now to FIG. 10, the prosthesis 110 is used to reconstruct the ossicular chain between the incus 30 and the stapes 34 when a portion of the long process 36 of the incus 30 is eroded or missing and the stapes superstructure is missing (i.e., only the footplate 42 of the stapes remains). The larger diameter first end 122 of the first coil 112 is placed over the intact portion of the long process 36. The distal end 154 of the piston 150 is placed on the footplate 42 of the stapes. Alternatively, when the footplate is immobile, the distal end of the piston can be placed through a footplate stapedostomy. The first and second coils 112, 152 can be adjusted in the length so that the prosthesis permits the incus 30 to maintain its anatomical orientation. In addition, the windings 118 of the first coil 112 may be adjusted relative to each other to better fit the incus. No crimping is required during the implantation. Referring to FIG. 11, the prosthesis 110 may also be cemented relative to the incus 30 and/or stapes footplate 42 with cement 40, generally as described above.

Figure 12:
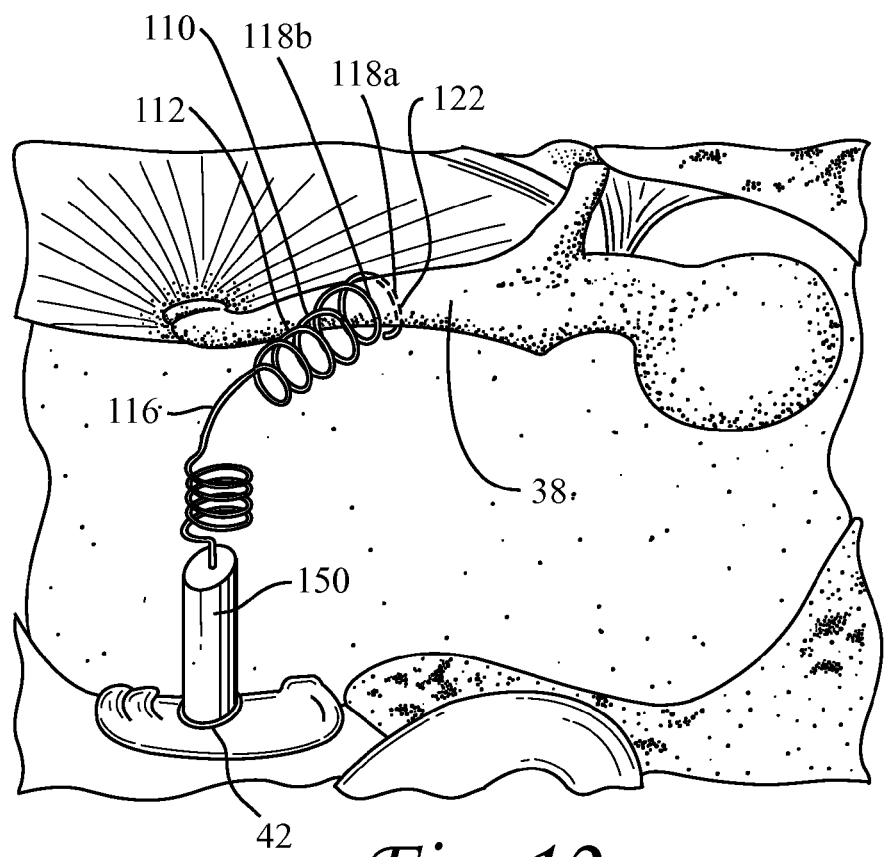
FIG. 12 illustrates implantation of the second embodiment of the ossicular prosthesis between the malleus and the stapes footplate.
Figure 13:
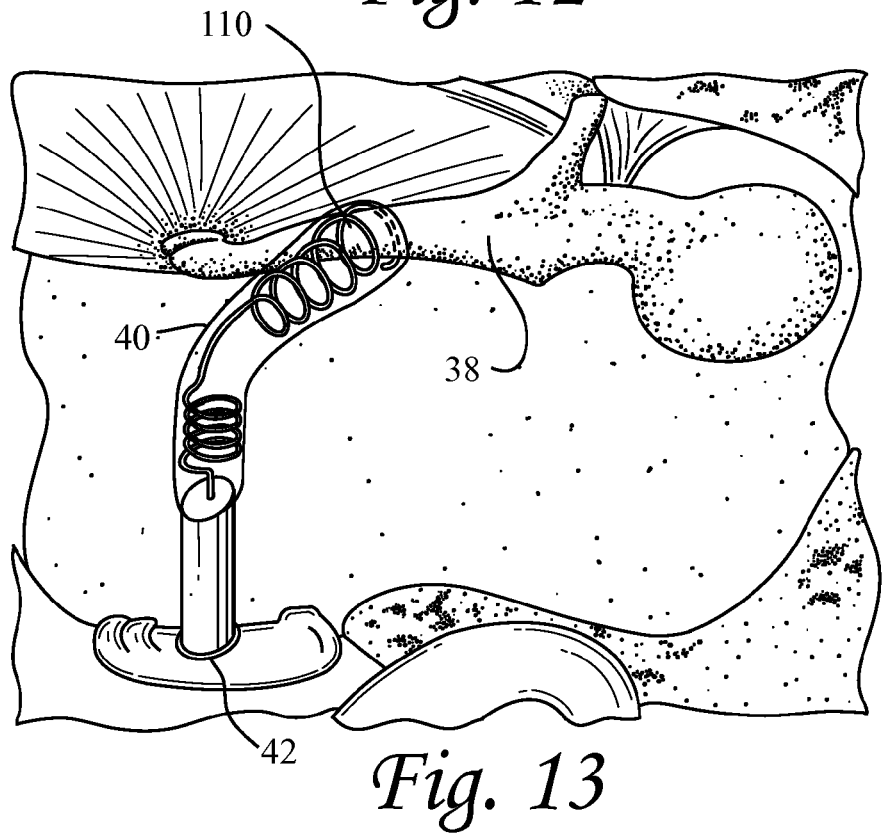
FIG. 13 illustrates the implanted prosthesis of FIG. 12 covered in a cement.

Turning now to FIG. 12, when both the incus and stapes superstructure are missing, the prosthesis 110 can be used to reconstruct the ossicular chain between the malleus 38 and the stapes footplate 42. The windings 118a, 118b at the larger diameter first end 122 of the first coil 112 are spread open and placed over the malleus 38. No crimping is required during implantation. The adjacent tympanic membrane is not disturbed. The piston 150 is placed on a mobile stapes footplate 42 or through a stapedostomy of an immobile stapes footplate 42. The windings 118a, 118b may need to be opened and the winding 116 (or strut) may need to be re-angled by the surgeon (e.g., $\alpha$=100° to 120°), or an embodiment of the prosthesis may be manufactured for such implantation with the windings opened and/or the strut set at the required angle. Referring to FIG. 13, the prosthesis 110 may also be cemented relative to the malleus 38 and/or stapes footplate 42 with cement 40, generally as described above.

Figure 14:
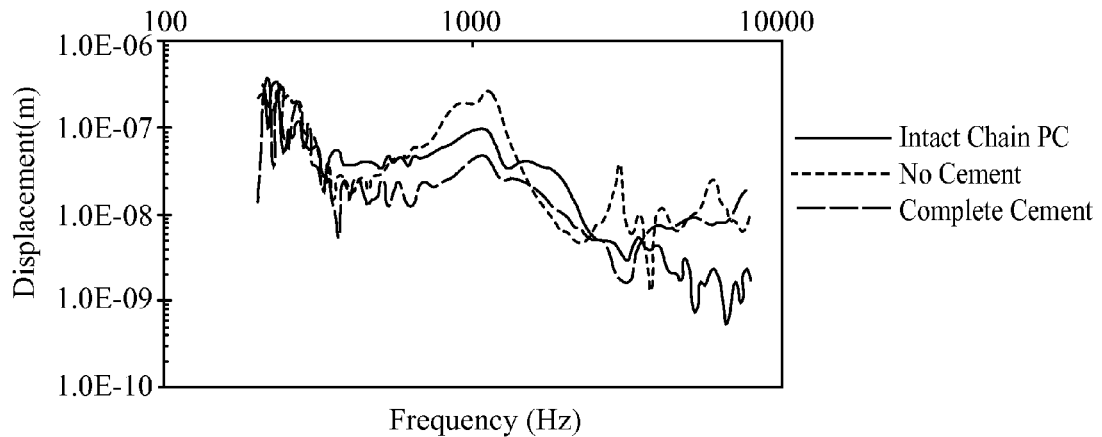
FIG. 14 graphs displacement versus frequency in response to a 100 dB SPL sound stimulus for laser doppler vibrometry measurements at the stapes for the implanted second embodiment of the invention, with and without cement, as compared to measurements of the intact ossicular chain, in a fresh frozen human temporal bone.
Figure 15:
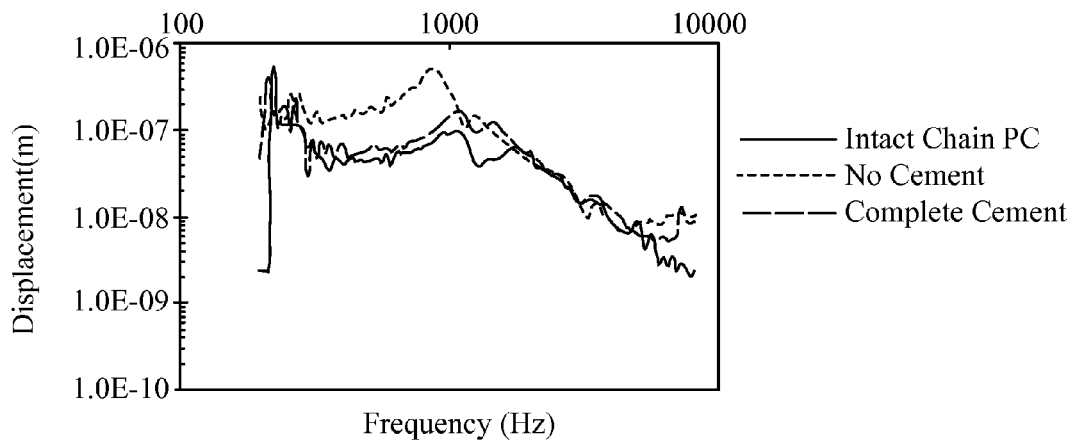
FIG. 15 graphs displacement versus frequency in response to a 100 dB SPL sound stimulus for laser doppler vibrometry measurements at the incus for the implanted second embodiment of the invention, with and without cement, in a fresh frozen human temporal bone.

Referring now to FIGS. 14 and 15, to test the responsiveness of the prosthesis 110, laser doppler vibrometry tests were performed comparing the prosthesis (without cement and in various states of cementing: pre-coat cement, proximal cement, and complete cement) to the responsiveness of an intact ossicular chain. The tests compared the displacement at various frequencies to a 100 dB SPL sound stimulus. Measurements were made at the stapes (FIG. 14) and at the incus (FIG. 15). It is initially evident that the measurements of the prosthesis, with and without cement, tracked the intact ossicular chain very well. The relative movement at the various frequencies indicate that the performance of the prosthesis in each of the implantable iterations, while slightly different, is very good.

Figure 16:
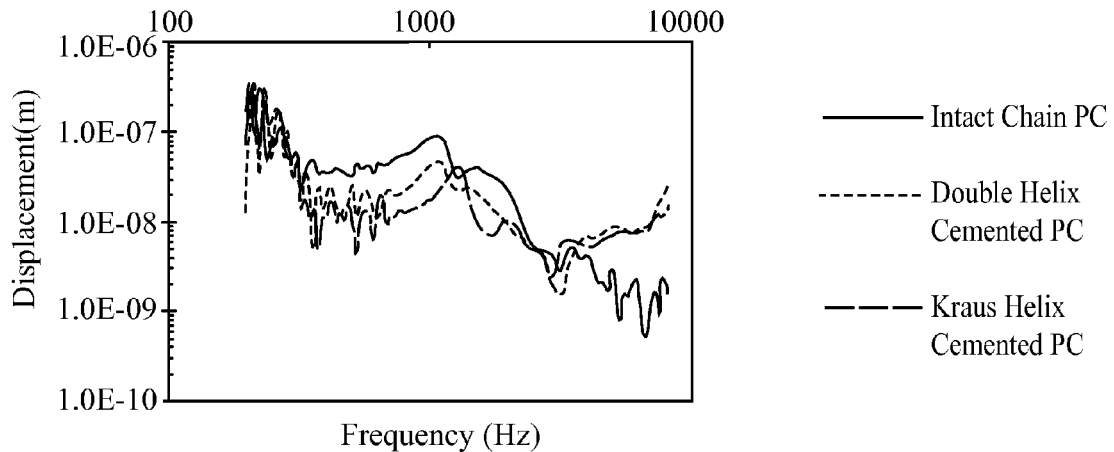
FIG. 16 graphs displacement versus frequency in response to a 100 dB SPL sound stimulus for laser doppler vibrometry measurements at the stapes for the implanted and cemented first and second embodiments of ossicular prostheses according to the invention.
Figure 17:
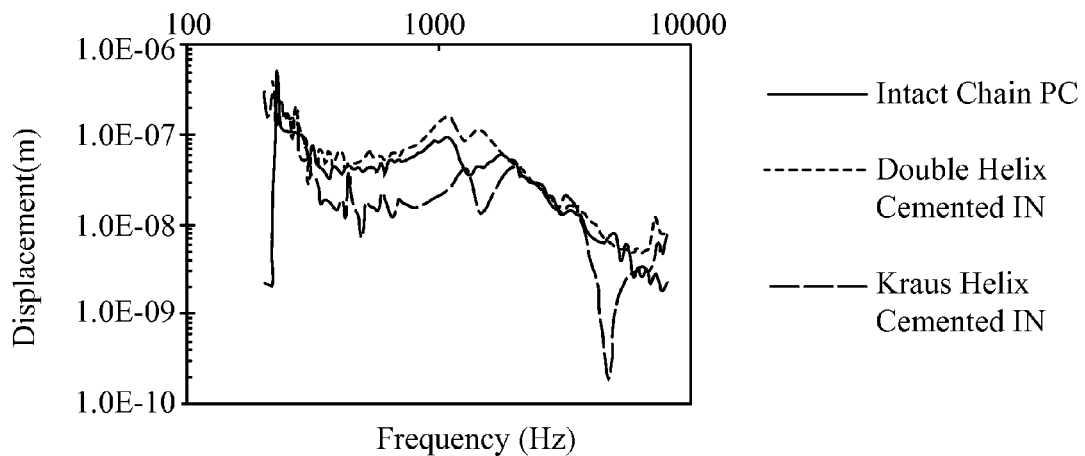
FIG. 17 graphs displacement versus frequency in response to a 100 dB SPL sound stimulus for laser doppler vibrometry measurements at the incus for the implanted and cemented first and second embodiments of ossicular prostheses according to the invention.

Referring now to FIGS. 16 and 17, an intact ossicular chain was compared to both prosthesis 10a (FIG. 2) and prosthesis 110 (FIG. 9A). Laser doppler vibrometry tests were performed comparing the intact ossicular chain to prostheses 10a and 110, both in their fully cemented form. Measurements were made at the stapes (FIG. 16) and at the incus (FIG. 17). It is initially evident that the measurements of the prosthesis, with and without cement, tracked the intact ossicular chain and each other very well.

Turning now to FIGS. 18 through 20, a third embodiment of an ossicular prosthesis 210 is shown. The prosthesis 210 includes a proximal conical helical coil 212 coupled to a bell head 214. The coil preferably includes six or seven windings of titanium wire (by way of example, and not by limitation, 35 gauge wire) with a proximal coil diameter of preferably 4.5 mm. The coil 212 defines a cone having a edge 217 oriented parallel to, and preferably offset from, the central axis $A_B$ of the bell head 214, and angled at, e.g., 60°, relative to diametrically opposite edge 219 of the coil. The coil 212 has a central axis Ac extending at an angle relative to axis $A_B$. The first end 222 of the coil 212 is optionally provided with one or more spikes 256. The spikes are preferably 0.2-0.5 mm in height. The spikes 256 may be provided directly on the coil (as shown) or provided to a separate element, such as a plate, which is then coupled to the first end of the coil (not shown). Referring to FIG. 21, the prosthesis is adapted for use when the incus and malleus are missing, but the stapes 34 is intact. The prosthesis 210 is implanted between the tympanic membrane 44 and the stapes capitulum 32 or crura of the stapes. If the superstructure of the stapes is missing, a piston can replace the bell head and be seated on the stapes footplate 32, such as shown in FIGS. 9A and 9B. The spikes 256 at the proximal end 222 of the coil facilitate retention of cartilage 46 between the proximal end of the coil and the tympanic membrane 44 or temporalis fascia graft. A cement (not shown) can also be used between the prosthesis and ossicular structure and/or over all or portions of the prosthesis 210.

Figure 22:
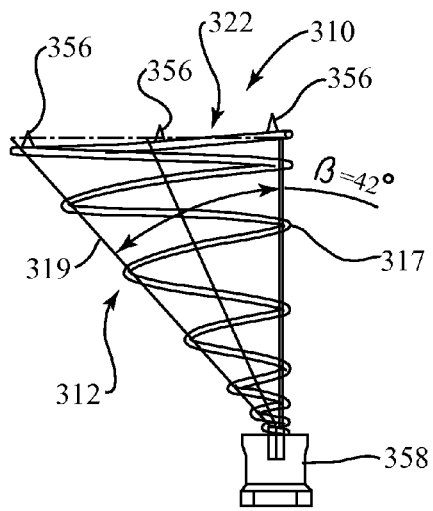
FIG. 22 is a side elevation of an alternate third embodiment of an ossicular prosthesis according to the invention.
Figure 23:
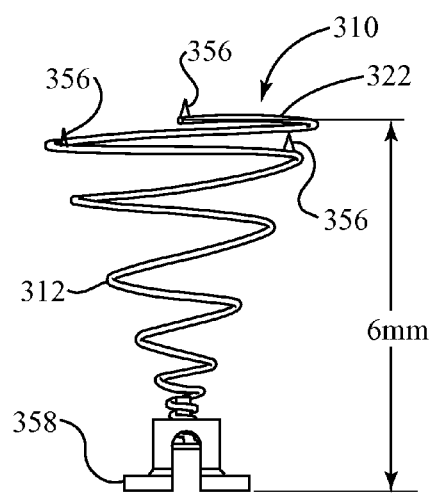
FIG. 23 is a view of the alternate third embodiment rotated 90° from FIG. 22.
Figure 24:
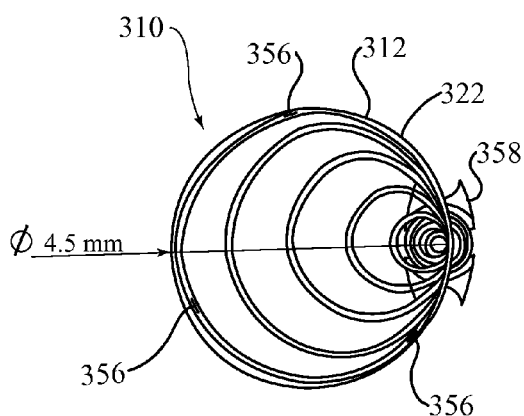
FIG. 24 is a top view of the alternate third embodiment of the invention.
Figure 25:
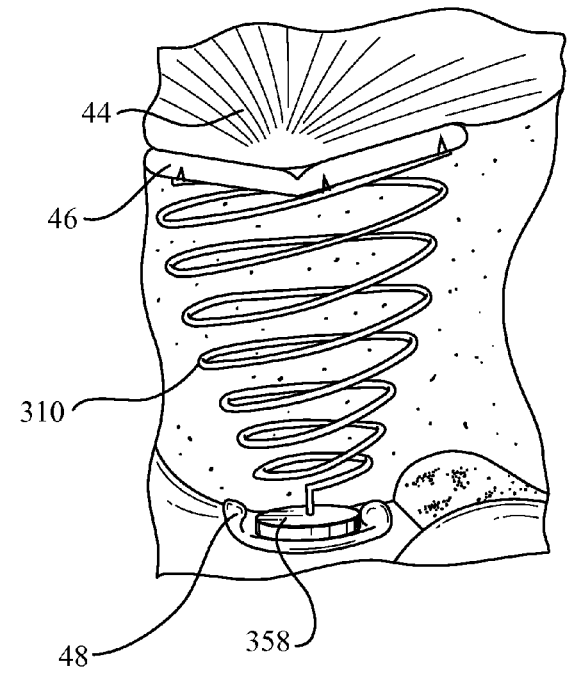
FIG. 25 illustrates implantation of the alternate third embodiment of the ossicular prosthesis between the tympanic membrane and the stapes footplate or oval window.

Turning now to FIGS. 22 through 24, a variation of the third embodiment of the prosthesis 310 is provided for use where the entire ossicular chain is missing. The prosthesis 310 is substantially similar in structure to prosthesis 210, but the coil 312 is longer (e.g., 6 mm compared to 3 mm for coil 212), the angle $\beta$ between edge 317 to edge 319 is smaller (e.g. $\beta$=42°), and the distal end is provided with a footplate shoe 358 (e.g., similar to a Dornhoffer shoe), rather than a bell head 214 (FIGS. 18 through 20). The first end 322 of the coil 312 is optionally provided with one or more spikes 356. The spikes are preferably 0.2 mm-0.5 mm in height. Referring to FIG. 25, the proximal end of the prosthesis is positioned against the tympanic membrane 44 or tissue graft, with cartilage 46 interposed therebetween, and the distal end of the prosthesis is seated against the footplate 48. The shoe provides increased surface area relative to the distal end of a piston in order to increase stability. A cement (not shown) can also be used between the prosthesis and ossicular structures and/or over all or portions of the prosthesis 310.

Figure 26:
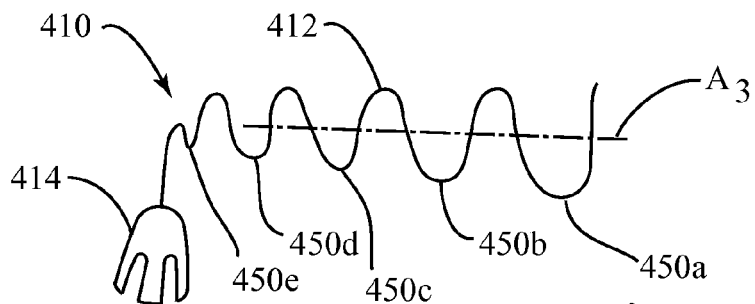
FIG. 26 is a side elevation view of a fourth embodiment of an ossicular prosthesis according to the invention.
Figure 27:
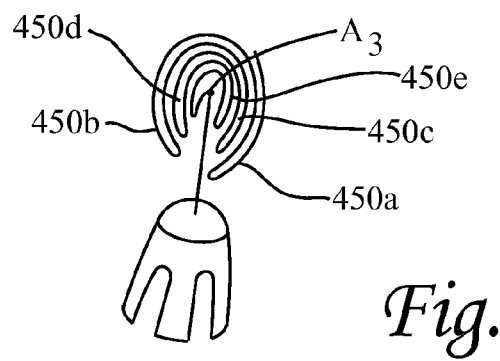
FIG. 27 is an end view of the fourth embodiment of FIG. 26.

While a helical conical coil is preferred for the various embodiments 10, 110, 210, 310, as it corresponds in shape to the bone and provides a self-locking function (even without cement), it is appreciated that non-helical coil structures can also be used. For example, turning now to FIGS. 26 and 27, a fourth embodiment of a prosthesis 410 is shown. The prosthesis 410 includes a wire structure 412 formed into a winding that corresponds in shape to the long process of the incus. The structure 412 includes a plurality of reverse turns (windings) 450 displaced along a long axis $A_3$ that, when placed over the long process, are adapted to wind around the long process of the incus in a generally helical manner. Each of the reverse turns 450 is greater than 180° and is sized such that it naturally engages the incus. Alternatively, the structure 412 can be made from a shape memory alloy that when heat activated above a transition temperature is adapted to transition in shape to causes the respective windings to decrease in diameter and engage the incus. The prosthesis is adjustable in length intraoperatively by altering the shape of the windings along the axis $A_3$. While the prosthesis 410 is shown with a bell head 414, it is appreciated that each of the prostheses described above can be implemented with the wire structure 412. In addition, the angle between axis $A_3$ and bell head 414 or other structure can also be adjusted intraoperatively.

Figure 28:
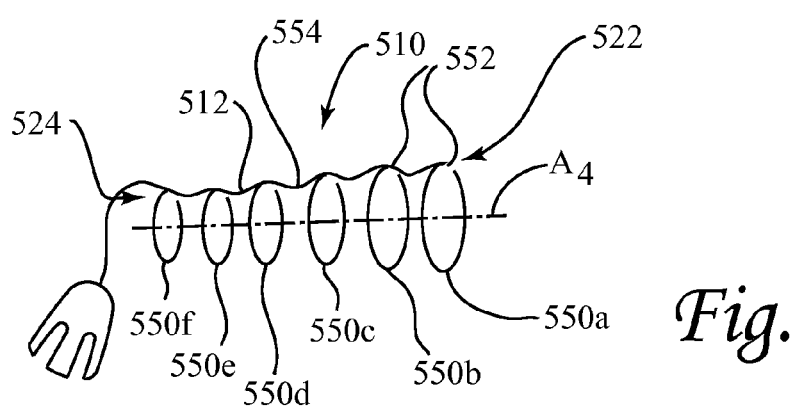
FIG. 28 is a side elevation view of a fifth embodiment of an ossicular prosthesis according to the invention.
Figure 29:
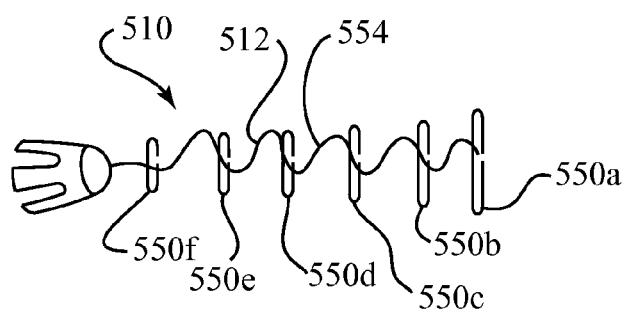
FIG. 29 is a top view of the fifth embodiment of FIG. 28.

By way of another example, referring now to FIGS. 28 and 29, a fifth embodiment of a prosthesis 510 is shown. The prosthesis includes a wire backbone 512 that is provided with a plurality of hoops (windings) 550a-550f spaced apart along an axis $A_4$. The wire backbone can be provided with bends, e.g., 554, any of which can be straightened or compressed to alter the length of the backbone along axis $A_4$. The hoops 550 (collectively) decrease in diameter from the first end 522 to the second end 524. The hoops 550 are preferably sized to anatomically fit the long process of the incus. Each of the hoops 550 preferably has a circumferential opening 552, permitting the hoops 550 to be adjusted in diameter thereat. The hoops 550 may be sized slightly smaller than the corresponding anatomy, and be adapted to spread apart (to increase diameter thereof) at the opening to fit snugly on the anatomy. In addition, the hoops 550 can be slightly larger than the anatomy and made from a shape memory alloy and thereby be adapted to decrease in diameter upon application of heat to better adapt to the structure to the anatomy for a snug fit. For purposes of the claims, the wire structures of FIGS. 26-29 are considered windings spaced apart along a longitudinal axis. In all the embodiments of the invention, the length of the prosthesis is adjustable intraoperatively. In addition, in all embodiments coupling either the malleus or incus to the stapes, the angle between the malleus or incus engaging portion and the stapedial engaging portion of the prosthesis can be adjusted intraoperatively.

Figure 30:
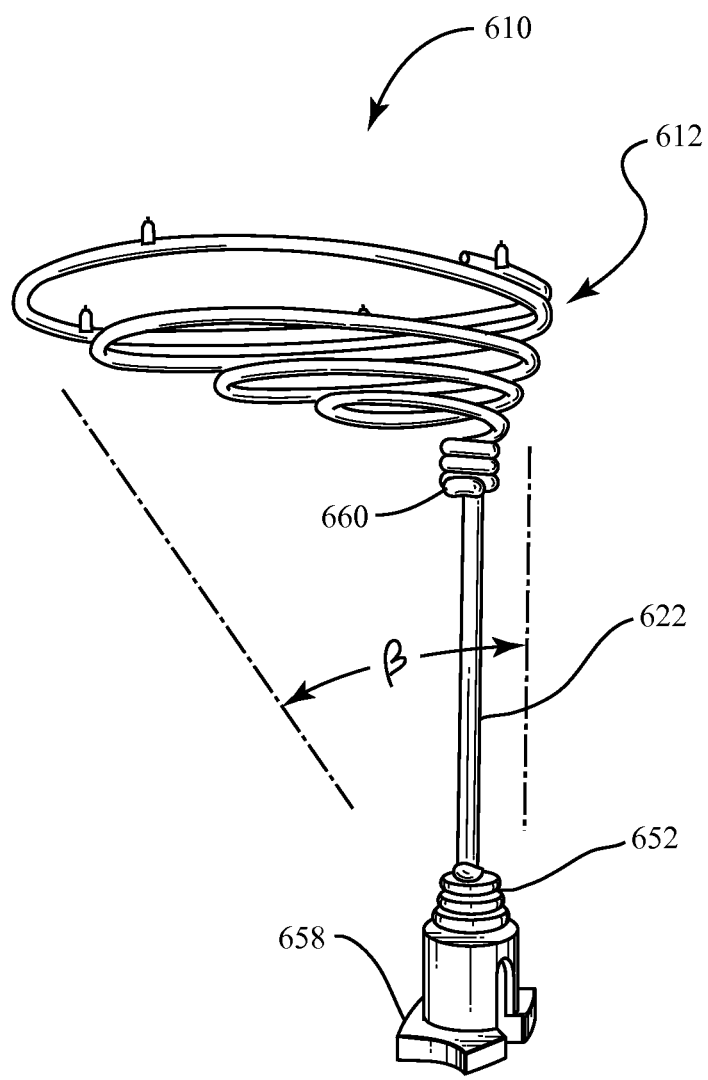
FIG. 30 is a side elevation view of a sixth embodiment of an ossicular prosthesis according to the invention.

Turning now to FIG. 30, a sixth embodiment of a prosthesis 610 according to the invention is shown. The prosthesis 610 is a TORP, for use when the malleus, incus, and stapes superstructure are absent. Prosthesis 610 includes a proximal helical conical coil 612 coupled to a rod 616 coupled to a shoe 658. The coil 612 includes fewer windings than in other embodiments designed for such use. By way of example, the coil 612 may include four helical windings. To accommodate the additional anatomical distance not supported by the shorter coil 612, the distal end of the coil is coupled, e.g., via a weld 660, to the proximal end of the preferably straight rod 622. The distal end of the rod 622 is coupled to the shoe 658. Optionally, a malleable secondary coil 652 is provided between the rod 622 and the shoe 658 to permit the rod 622 and coil 652 to be plastically deformed relative to each other. In this embodiment, the prosthesis 610 preferably defines the same angle β as in the embodiment shown in FIG. 22 so as to properly accommodate the anatomy. It is appreciated that the features of a shorter coiled portion in combination with a rod can likewise be used to form similar alternate embodiments to those shown and described herein.

It is also appreciated that the invention comprises a kit for ossicular reconstruction including a plurality of prostheses. The prostheses includes (i) prosthesis 10 (or variants thereof) with coil and bell head for incudo-stapedial reconstruction or mallear-stapedial interposition where the stapes superstructure is present, (ii) prosthesis 110 (or variants thereof) with coil and piston for incudo-stapedial or mallear-stapedial interposition (1) where the stapes superstructure is missing and (2) where the stapes footplate is mobile or immobile, and (iii) prosthesis 210 (or variants thereof) with coil and parallel bell head for tympanic membrane-stapes interposition when the incus and malleus are missing or prosthesis 310 (or variants thereof) with coil and shoe for tympanic membrane-stapes footplate or oval window interposition when the incus, malleus, and stapes superstructure are missing. The prostheses of the kit may include an alternate wire structure with spaced apart windings, as generally discussed above with respect to FIGS. 26-29, or the shorter coil and rod structure as shown in FIG. 30. The kit provides prostheses than are adapted to reconstruct any ossicular deficit, and each of the prostheses is adjustable by the surgeon so as to be adapted to a patient's anatomy.

Figure 31:
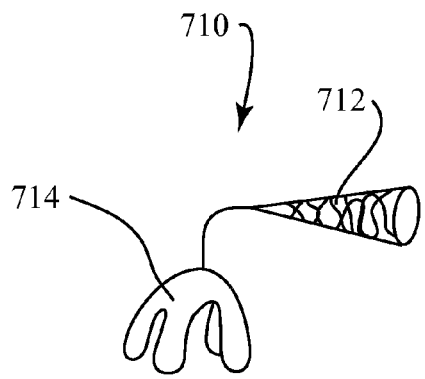
FIG. 31 is a side elevation of a seventh embodiment of an ossicular prosthesis according to the invention
Figure 32:
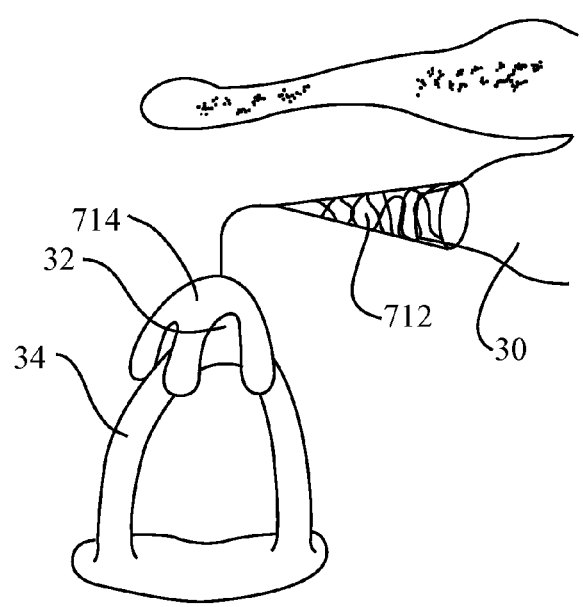
FIG. 32 illustrates implantation of the seventh embodiment of the ossicular prosthesis between the long process of the incus and the stapes capitulum.

Referring now to FIGS. 31 and 32, a seventh embodiment of ossicular prosthesis 710 is shown. Rather than a wire-form structure with windings (as previously described), such prosthesis 710 includes a proximal end having a conical mesh-form 712 for placement over the incus 30 and a distal end including a bell head 714 for placement on the capitulum 32 of the stapes 34. The mesh-form is suitable as an armature for receiving cement to fix the prosthesis to the incus.

Figure 33:
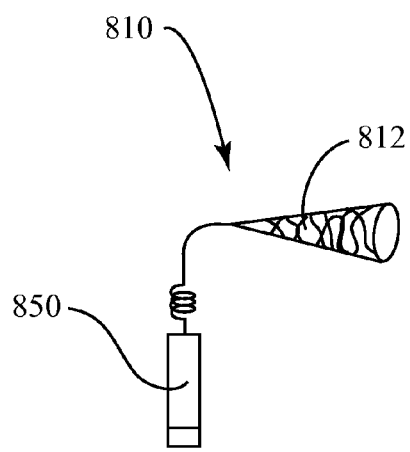
FIG. 33 is a side elevation of an eighth embodiment of an ossicular prosthesis according to the invention.

Referring to FIG. 33, an eighth embodiment of a prosthesis 810 is shown. The prosthesis has a proximal end including a conical mesh-form 812 for receiving the incus and a distal piston 850 for placement on or through the stapes footplate. The mesh-form is suitable as an armature for receiving cement to fix the prosthesis to the incus.

Figure 34:
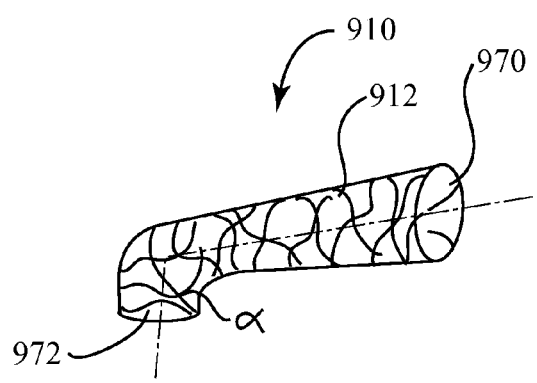
FIG. 34 is a side elevation of a ninth embodiment of an ossicular prosthesis according to the invention.

Referring to FIG. 34, a ninth embodiment of a prosthesis 910 is shown. The prosthesis 910 defines a mesh-form sleeve 912 having a proximal end with a first opening 970 for receiving the incus, and a distal end with a second opening 972 for receiving the stapes superstructure. The first and second openings 970, 972 are preferably oriented substantially transverse to each other, with central axes through each oriented relative to each other at angle α, as defined above with respect to FIGS. 1A and 2. The mesh-form sleeve is suitable as an armature for receiving cement to fix the prosthesis to the incus.

There have been described and illustrated herein several embodiments of an ossicular prosthesis and a methods of implanting the same. While particular embodiments of the invention have been described, it is not intended that the invention be limited thereto, as it is intended that the invention be as broad in scope as the art will allow and that the specification be read likewise. Thus, while particular structural materials and cements have been disclosed, it will be appreciated that other structural materials and cements can be used as well. In addition, while particular dimensions and angles have been disclosed, it will be understood that other dimensions and angles suitable for the intended purpose can be used. Also, while various alternate structures to helical coils have been disclosed, it is appreciated that other structures with multiple windings can also be used. Further, features and particulars of the various embodiments can be used interchangeably with the other embodiments described. Moreover, while various wire form structures are described: coil, reverse windings, and windings displaced along a backbone, it is appreciated that such wire form structures can be formed by other similarly malleable open metalforms including ribbon-forms. For purposes of the claims, a ribbon is a flat wire. It will therefore be appreciated by those skilled in the art that yet other modifications could be made to the provided invention without deviating from its spirit and scope as claimed.

What is claimed is:

1. An ossicular prosthesis for implantation in a middle ear of a human for reconstruction of an ossicular chain, the middle ear including a tympanic membrane with tissue and the ossicular chain of the middle ear including a stapes, said prosthesis comprising:
   a) an open-wound helical conical wire-form coil having a first end and a second end, said first end includes a first winding defining a first diameter and said second end includes a second winding defining a smaller second diameter, and at least two windings between said first and second windings, said coil continuous between said first and second windings, said first end of said coil capable of being positioned directly against the tissue;
   b) an engagement structure including one of a bell head, a piston, and a shoe for engaging a portion of the stapes; and
   c) a connecting element coupling said second end of said coil to said engagement structure in a fixed orientation, wherein said ossicular prosthesis is of a suitable size and material for implantation into the middle ear with said prosthesis extending from the tympanic membrane to the portion of the stapes to stably retain the prosthesis between the tympanic membrane and the portion of the stapes to at least partially reconstruct the ossicular chain.

2. An ossicular prosthesis according to claim 1, wherein: said engagement structure defines an axis, and said helical conical coil defines a cone in which one side of said cone is parallel with said axis and an opposite side of said cone is angled at an angle relative to said axis.

3. An ossicular prosthesis according to claim 2, wherein: said angle is 42°.

4. An ossicular prosthesis according to claim 2, wherein: said one side is situated in alignment with said axis.

5. An ossicular prosthesis according to claim 2, wherein: said cone defines a longitudinal axis extending between the center of the windings, and said longitudinal axis of said cone is not parallel to said axis of said engagement structure.

6. An ossicular prosthesis according to claim 1, wherein: a length of said coil is at least 3 mm.

7. An ossicular prosthesis according to claim 6, wherein: said second diameter is 4.5 mm.

8. An ossicular prosthesis according to claim 1, wherein: said coil defines a longitudinal axis extending between the center of the windings, and said prosthesis is adapted such that said longitudinal axis extends in a direction from the tympanic membrane to the portion of the stapes.

9. An ossicular prosthesis according to claim 1, wherein: said second diameter is 4.5 mm.

10. An ossicular prosthesis according to claim 1, wherein: said first winding is provided with spikes.

11. An ossicular prosthesis according to claim 10, wherein: said spikes are 0.2 mm-0.5 mm in height.

12. An ossicular prosthesis according to claim 1, wherein: a longitudinal axis extends through said wire-form coil, and said wire-form coil is plastically deformable to adjust at least one of (i) a length of said wire-form coil along said longitudinal axis and (ii) a diameter of at least one winding.

13. An ossicular prosthesis for implantation in a middle ear of a human for reconstruction of an ossicular chain, the middle ear including a tympanic membrane with tissue and the ossicular chain of the middle ear including a stapes, said prosthesis comprising:
   a) an open-wound helical conical coil having a first end and a second end, said first end includes a first winding defining a first diameter and said second end includes a second winding defining a smaller second diameter, and at least two windings between said first and second windings, said coil continuous between said first and second windings, said first end of said coil capable of being positioned directly against the tissue;
   b) an engagement structure including one of a bell head, a piston, and a shoe for engaging a portion of the stapes, said engagement structure having an axis; and
   c) a connecting element coupling said second end of said coil to said engagement structure in a fixed orientation,
      a longitudinal axis extending between the center of the windings of said coil, said longitudinal axis of said coil is not parallel to said axis of said engagement structure,
      wherein said coil is plastically deformable to adjust at least one of (i) a length of said wire-form coil along said longitudinal axis and (ii) a diameter of at least one winding, and
      wherein said ossicular prosthesis is of a suitable size and material for implantation into the middle ear with said prosthesis extending from said tympanic membrane to the portion of the stapes to at least partially reconstruct the ossicular chain.

14. An ossicular prosthesis according to claim 13, wherein: said coil includes a first side extending parallel to said axis of said engagement structure and an opposite second side extending at an angle relative to said first side.

15. An ossicular prosthesis according to claim 14, wherein: said coil defines an angle of 60°.

16. An ossicular prosthesis according to claim 15, wherein: a length of said coil is at least 3 mm.

17. An ossicular prosthesis according to claim 16, wherein: said second diameter is 4.5 mm.

* * * * *